(12) United States Patent
Farkas et al.

(10) Patent No.: US 6,450,949 B1
(45) Date of Patent: Sep. 17, 2002

(54) ENDOSCOPE

(75) Inventors: Richard Farkas, Bloomfield Hills; Richard Fisher, Ann Arbor; Steven Henke, Canton, all of MI (US)

(73) Assignee: Inner Vision Imaging, Inc., Farmington Hills, MI (US)

( * ) Notice: Subject to any disclaimer, the term of this patent is extended or adjusted under 35 U.S.C. 154(b) by 162 days.

(21) Appl. No.: 09/706,059

(22) Filed: Nov. 3, 2000

Related U.S. Application Data

(63) Continuation-in-part of application No. 09/608,321, filed on Jun. 30, 2000.

(51) Int. Cl.$^7$ .................................................. A61B 1/00
(52) U.S. Cl. .................... 600/168; 600/121; 600/130
(58) Field of Search ................................ 600/130, 167, 600/168, 173, 106, 108, 109, 121, 473, 475; 359/696

(56) References Cited

U.S. PATENT DOCUMENTS

| | | | |
|---|---|---|---|
| 3,090,378 A | * 5/1963 | Sheldon et al. ............. 385/117 |
| 3,561,432 A | * 2/1971 | Yamaki et al. ........... 356/241.5 |
| 3,819,267 A | * 6/1974 | Kawahara .................... 356/21 |
| 4,136,939 A | * 1/1979 | Abe ........................... 396/111 |
| 4,269,485 A | 5/1981 | Yamashita et al. |
| 4,300,812 A | 11/1981 | Nakahashi |
| 4,312,572 A | 1/1982 | Yamashita et al. |
| 4,385,810 A | 5/1983 | Hamou |
| 4,639,772 A | 1/1987 | Sluyter et al. |
| 4,664,486 A | 5/1987 | Landre et al. |
| 4,666,262 A | 5/1987 | Zobel |
| 4,704,007 A | 11/1987 | Landre et al. |
| 4,821,117 A | 4/1989 | Sekiguchi .................... 358/98 |
| 4,905,082 A | 2/1990 | Nishigaki et al. |
| 5,255,087 A | 10/1993 | Nakamura et al. ............ 358/98 |
| 5,396,366 A | 3/1995 | Brown et al. |
| 5,418,645 A | 5/1995 | Coath et al. |
| 5,532,873 A | 7/1996 | Dixon |
| 5,582,576 A | 12/1996 | Hori et al. |
| 5,659,642 A | 8/1997 | King et al. |
| 5,719,700 A | 2/1998 | Corcuff et al. |
| 5,737,121 A | 4/1998 | Dixon |
| 5,742,419 A | 4/1998 | Dickensheets et al. |
| 5,745,165 A | * 4/1998 | Atsuta et al. ................. 348/65 |
| 5,788,639 A | 8/1998 | Zavislan et al. |
| 5,817,014 A | * 10/1998 | Hori et al. .................... 348/65 |
| 5,836,869 A | 11/1998 | Kudo et al. ................. 600/173 |
| 5,836,877 A | 11/1998 | Zavislan |
| 5,842,972 A | * 12/1998 | Wulfsberg .................. 600/133 |
| 5,863,287 A | 1/1999 | Segawa ...................... 600/121 |
| 5,910,816 A | 6/1999 | Fontenot et al. |

(List continued on next page.)

Primary Examiner—John P. Leubecker
(74) Attorney, Agent, or Firm—Gifford, Krass, Groh, Sprinkle, Anderson & Citkowski, P.C.

(57) ABSTRACT

An endoscope assembly is disclosed having a housing adapted to be manipulated by medical personnel, such as a surgeon. An elongated lens tube has one end secured to the housing while the free end of the lens tube is adapted for insertion into a cavity of a body. At least one, and preferably several, lens assemblies are longitudinally slidably mounted within the lens tube and movable between longitudinally spaced positions within the lens tube. A drive mechanism is mounted to the housing and mechanically coupled to each lens assembly to move the lens assemblies longitudinally within the lens tube independently of one another. In doing so, the lens assemblies provide varying degrees of magnification between low or macroscopic magnification and microscopic magnification at the free end of the lens tube. A stage is also detachably secured over the lens tube and has a transparent window across its end adjacent the free end of the lens tube. In use, the stage window is positioned against target tissue within a human cavity while the lens assemblies are longitudinally displaced within the lens tube to obtain the desired magnification. Strands extending through and/or connected to the lens groups are used to longitudinally displace the lens groups.

30 Claims, 7 Drawing Sheets

U.S. PATENT DOCUMENTS

| | | |
|---|---|---|
| 5,995,867 A | 11/1999 | Zavislan et al. |
| 5,997,472 A | 12/1999 | Bonnell et al. ............. 600/109 |
| 6,007,482 A | 12/1999 | Madni et al. |
| 6,013,025 A | 1/2000 | Bonne et al. ................ 600/160 |
| 6,028,622 A | 2/2000 | Suzuki ........................ 348/65 |
| 6,059,721 A | 5/2000 | Rudischhauser et al. ..... 600/167 |

* cited by examiner

ENDOSCOPE

CROSS-REFERENCE TO RELATED APPLICATIONS

This is a continuation-in-part of U.S. patent application Ser. No. 09/608,321, filed Jun. 30, 2000, and entitled "Endoscope."

BACKGROUND OF THE INVENTION

I. Field of the Invention

The present invention relates generally to medical instruments and, more particularly, to an endoscope.

II. Discussion of Related Art

Laparoscopic surgery has enjoyed increasing acceptance, particularly for surgery involving the abdominal cavity. In such surgery, one or more incisions are made through the patient's skin. Thereafter, various medical instruments, including endoscopes, are inserted through the incisions and into a body cavity, such as the abdominal cavity.

In order for the surgeon to see into the abdominal cavity, the surgeon typically uses an endoscope which is inserted through a cannula and into the abdominal cavity. The previously known endoscopes typically comprise an elongated tube having one or more fixed lenses. These lenses provide an optical view of the interior of the body cavity to an eyepiece or other display means accessible to the surgeon outside the body. Illumination for the endoscope is typically provided by optical fibers which extend along the length of the endoscope and form a ring around the outer periphery of the free end of the endoscope. The opposite ends of the optical fibers are connected to a light source.

These previously known endoscopes, however, have all suffered from a number of disadvantages. Perhaps the most significant disadvantage of these previously known endoscopes is that, since the optical lenses are fixed within the endoscope, the angular magnification for the endoscope remains constant. Typically, these previously known endoscopes utilize lenses which provide low or macroscopic magnification (hereafter collectively referred to as macroscopic magnification) within the body cavity so that a relatively wide field of view of the body cavity is obtained.

In many situations, however, it would be desirable for the endoscope to provide microscopic magnification of organs contained within the body cavity. For example, in certain situations where cancerous growths within body organs are suspected, the macroscopic magnification provided by the previously known endoscopes is insufficient to examine the organ tissue in sufficient detail to determine whether the tissue abnormality is cancerous or benign. As a result, it has been necessary for the surgeon to perform a biopsy of the tissue, and, in many cases entirely remove the tissue, for subsequent pathological examination outside the body.

The removal of biological tissue from the body and subsequent pathological examination outside the body suffers from two important disadvantages. First, in the event that the organ abnormality is benign, the biopsy and possible removal of the entire organ from the body results in unnecessary harm and even loss of organ function to the patient. Second, since the subsequent pathological examination of the body tissue oftentimes occurs long after the end of the operation, in the event that the pathological examination reveals a cancerous growth within the body tissue, it is oftentimes necessary for the surgeon to re-enter the body cavity and remove additional body tissue in an attempt to completely eradicate the cancer. This disadvantageously, however, subjects the patient to a second operation.

There have been previously known endoscopes which utilize movable lens groups to vary the image between microscopic and macroscopic magnification. These prior devices, however, have used complex systems for moving the lenses which disadvantageously increase the overall diameter of the endoscope.

SUMMARY OF THE PRESENT INVENTION

The present invention provides an endoscope for use in laparoscopic surgery which overcomes all of the above-mentioned disadvantages of the previously known devices.

In brief, the endoscope of the present invention comprises a housing which is adapted to be held by a robotic arm or manipulated by hand by the surgeon or other medical personnel. An elongated lens tube has one end secured to the housing. An elongated tubular stage is then removably secured over the lens tube and the stage and lens tube are adapted for insertion into the body cavity.

Unlike the previously known endoscopes, in addition to one or more fixed lens groups, at least one and preferably three lens assemblies are longitudinally slidably positioned within the lens tube. Drive means, such as stepping motors, contained within the housing are mechanically connected to each movable lens assembly in order to longitudinally displace the lens assemblies within the lens tube. In doing so, the optical magnification achieved by the lens assemblies in the endoscope can be varied between macroscopic magnification and microscopic magnification. Macroscopic magnification is utilized to provide an optical view for the surgeon of a relatively wide area within the body cavity while, conversely, microscopic magnification is utilized to examine target body tissues.

The stage is also longitudinally movable with respect to the lens tube between an extended and a retracted position by drive means contained within the endoscope housing. A transparent optical window is disposed across the free end of the stage and this window is in alignment with the optical system of the lens tube. Liquid, preferably a saline solution, is contained between the end of the lens tube and the window on the stage to eliminate refractive errors between the lens tube and the stage.

The lens contained within the lens tube and housing is preferably a confocal lens system. As such, with the stage window positioned against the target body tissue, longitudinal displacement of the stage relative to the lens tube provides a microscopic image through the endoscope at different tissue depths.

The ability to provide microscopic imaging of internal organs permits in vivo pathological examination of internal organs without the necessity of a biopsy. Furthermore, to enhance the imaging of the microscopic images, preferably infrared radiation is provided directly through the lens tube and stage window to the tissue. Any conventional source of infrared illumination can be utilized, but preferably a diode laser is utilized.

In the preferred embodiment of the invention, the optical images through the endoscope are digitized and coupled as an input signal to a computer system. The computer system, in turn, communicates the digitized images via a network and/or telephone lines to a pathologist remote from the patient. Consequently, the pathologist is capable of viewing the images through the endoscope on a real-time basis. Since the endoscope of the present invention enables real-time pathological examination of suspect tissue, unnecessary biopsies and/or organ removal is prevented.

Unlike the previously known endoscopes with movable lens groups, the present invention utilizes small strands extending through and/or connected with the lens groups in the endoscope so that longitudinal displacement of this strand longitudinally displaces the lens group associated with the strand. These strands advantageously do not increase the overall diameter of the endoscope.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which:

FIG. 4 is a longitudinal sectional view of a portion of the preferred embodiment of the present invention;

DETAILED DESCRIPTION OF A PREFERRED EMBODIMENT OF THE PRESENT INVENTION

Figure 1:
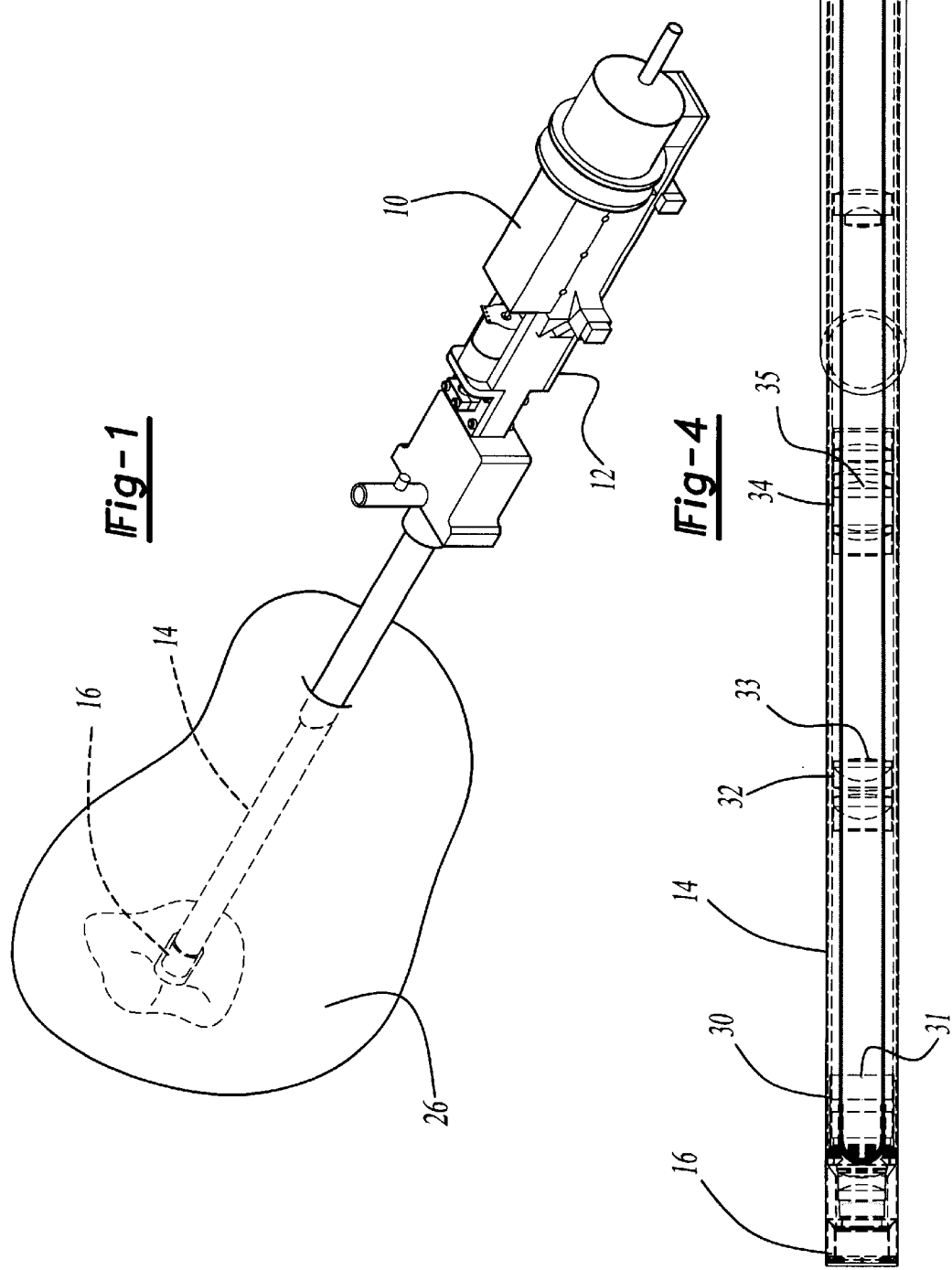
FIG. 1 is a perspective view illustrating a preferred embodiment of the present invention.
Figure 2:
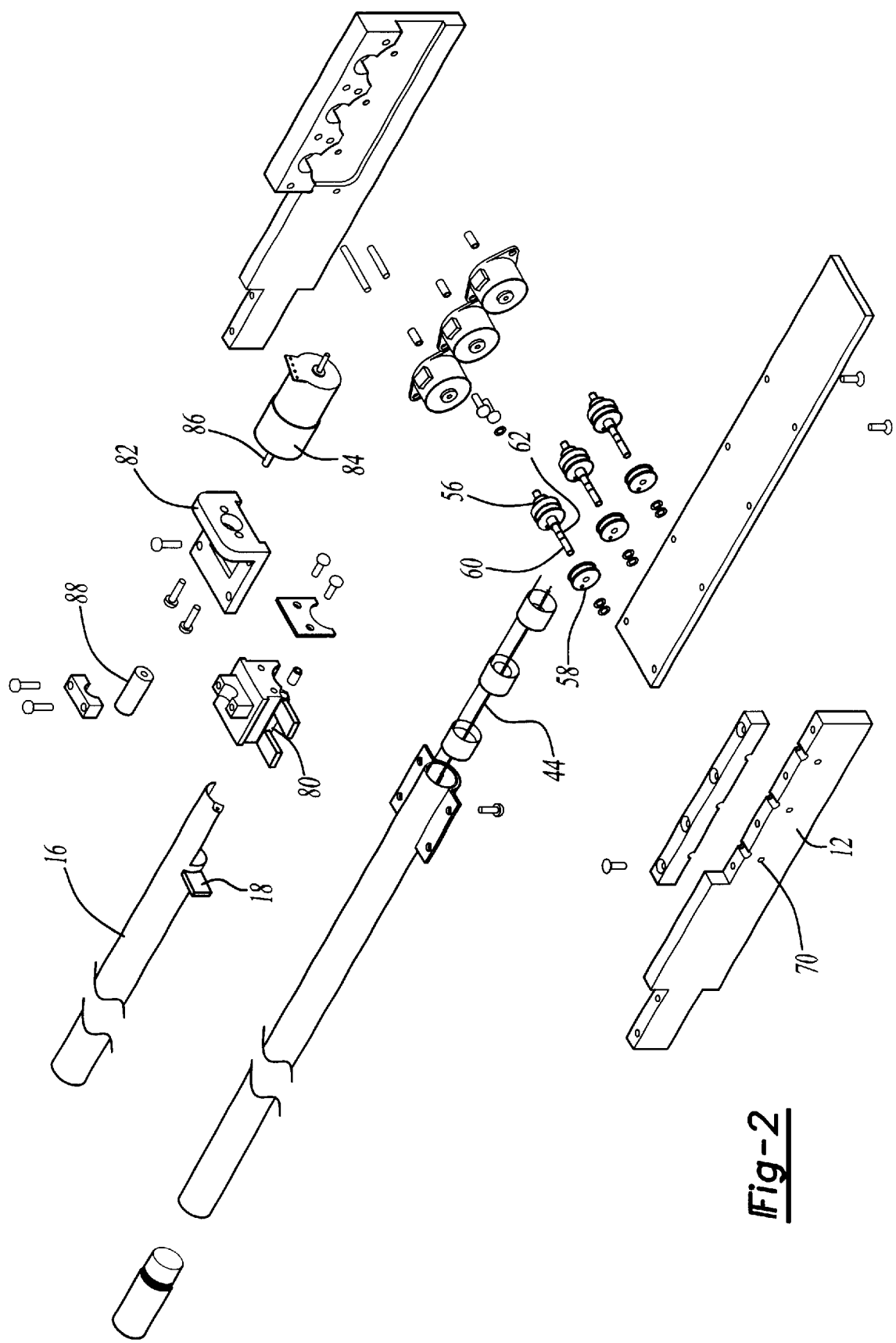
FIG. 2 is an exploded view illustrating a preferred embodiment of the present invention.
Figure 3:
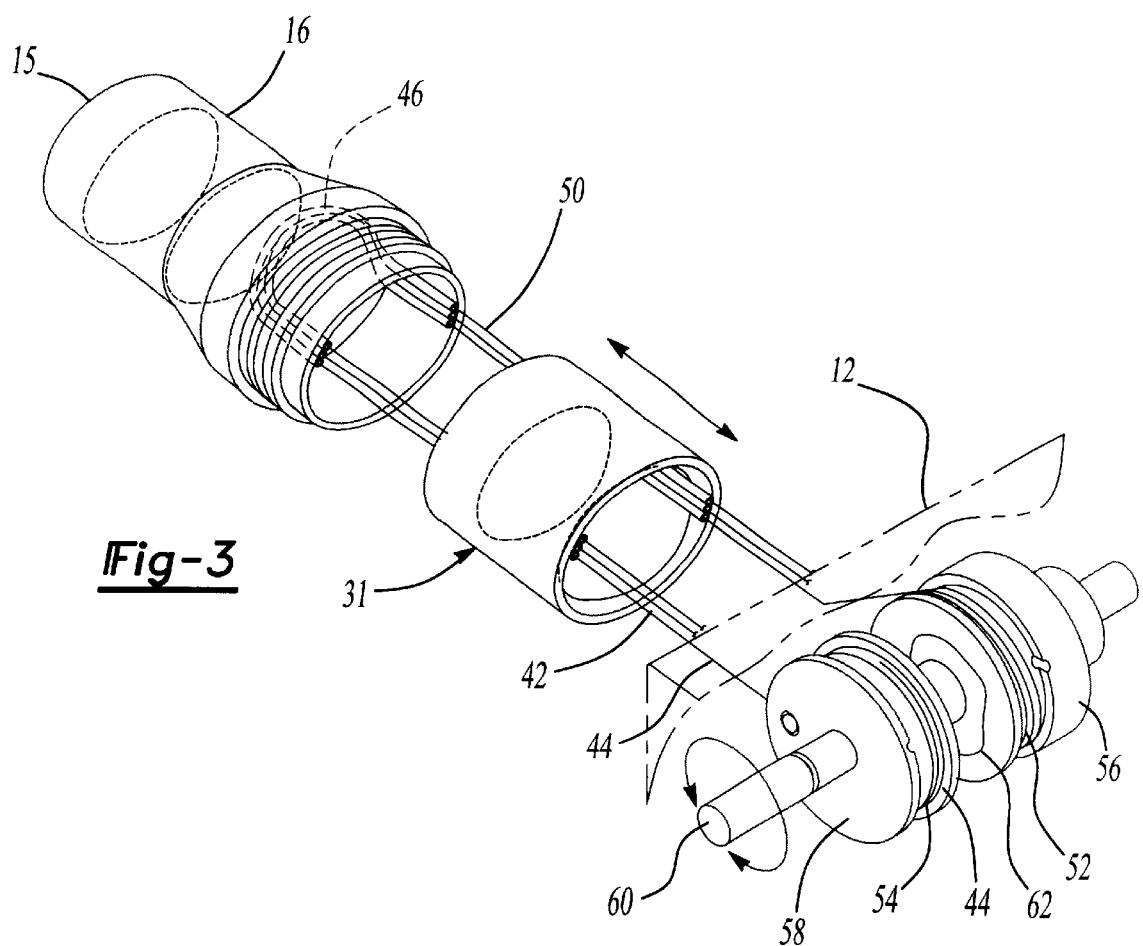
FIG. 3 is a perspective diagrammatic view illustrating a portion of the preferred embodiment of the present invention and with portions removed for clarity.

With reference first to FIGS. 1 and 3, a first preferred embodiment of the endoscope 10 of the present invention is there shown and comprises a housing 12 dimensioned to be hand held by medical personnel. An elongated lens tube 14 is secured to and extends outwardly from the housing 12. An elongated tubular stage 16 is open at one end and has a transparent window 20 (FIG. 6) disposed across its opposite end. The stage 16, furthermore, is dimensioned to be slidably received over the free end 15 of the lens tube 14 and detachably secured to the housing 12 by a bayonet coupling 18 (FIG. 2). Furthermore, with the stage 16 secured to the housing 12, the stage and lens tube are adapted for insertion into a body cavity 26.

Figure 8:
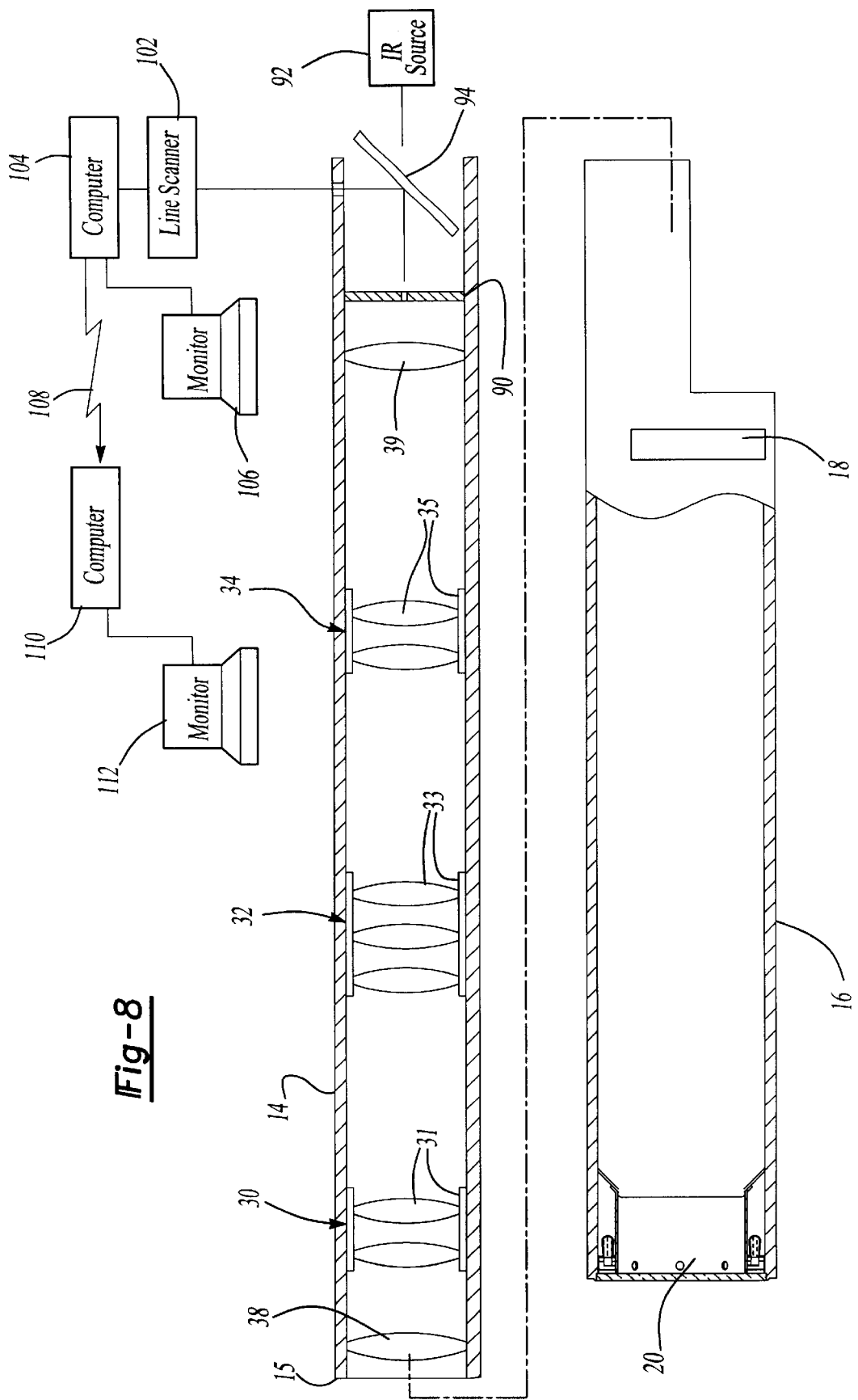
FIG. 8 is a longitudinal sectional exploded view illustrating the preferred embodiment of the present invention.

With reference now to FIGS. 3, 4 and 8, the endoscope 10 further comprises at least one, and preferably three moveable lens groups 30, 32 and 34. Each lens group 30, 32 and 34 is secured within its own support tube 31, 33 and 35, respectively, and these lens support tubes 31, 33 and 35 are longitudinally slidably mounted within the lens tube 14 so that the lens groups 30, 32 and 34 are movable relative to each other. Additionally, the endoscope 10 preferably includes a fixed objective lens 38 adjacent its free end 15 of the lens tube 14 as well as a focusing lens 39 spaced from the objective lens 34.

The mechanism to longitudinally displace the lens groups 30, 32 and 34 within the lens tube 14 are substantially identical to each other. Consequently, the longitudinal displacement mechanism will be described in detail only with respect to the lens group 30, it being understood that a like description shall also apply to the other lens groups 32 and 34. With reference then to FIG. 3, a first portion 42 of an elongated strand 44 extends through the lens tube 14 and through a generally U-shaped bearing tube 46 adjacent the free end 15 of the lens tube 14. This portion 42 of the strand 44 is secured to the lens support tube 31 in any conventional fashion.

A second portion 50 of the strand 44 extends back through the lens tube 14 and slidably through openings formed in the lens group 30 so that the free ends 52 and 54 of the strand 44 are contained within the housing 12. The strand 44, furthermore, is formed of a flexible non-elastic material, such as Nitinol.

With reference still to FIG. 3, the free ends 52 and 54 of the strand 44 are respectively secured to two drums 56 and 58 rotatably mounted in the housing 12. The ends 52 and 54 of the strand 44, furthermore, are secured to the drums 56 and 58 so that rotation of the drums 56 and 58 will wind the strand ends 52 and 54 in opposite directions. Consequently, rotation of the drums 56 and 58 in unison with each other longitudinally displaces the first portion 44, and thus the first lens group 30, in the lens tube 14 in a direction dependent upon the direction of rotation of the drums 56 and 58.

Since the strand 44 is secured to its associated lens group 30 and extends through openings in the outer periphery of the other lens groups, the strands, i.e. the moving mechanism for the lens groups, do not increase the overall diameter of the lens tube 14. Consequently, with the present invention, it is unnecessary to increase the size of the patient incision.

The drum 58 is preferably rotatably mounted on a shaft 60 which is secured to the second drum 56 so that the drums 56 and 58 can rotate slightly relative to each other. A torsion spring 62 is then preferably mechanically connected between the drums 56 and 58 and this torsion spring 62 imposes a tension on the strand 44 to eliminate any slack which may be present in the strand 44. The torsion spring 62 thus enables precise movement of the lens group 30 upon rotation of the drums 56 and 58.

Figure 7:
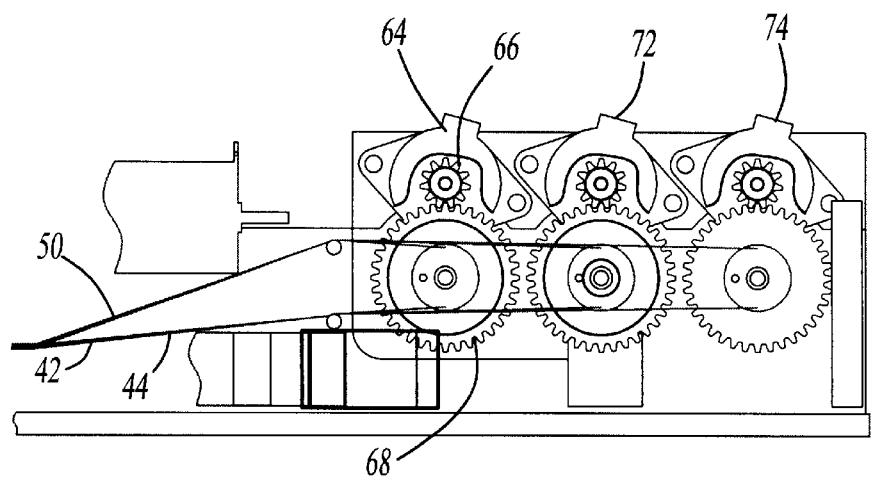
FIG. 7 is a fragmentary side diagrammatic view illustrating a portion of the preferred embodiment of the present invention.

Any conventional means may be utilized to rotatably drive the drums 56 and 58 and thus longitudinally displace the lens group 30. However, as best shown in FIG. 7, in the preferred embodiment of the invention, a stepping motor 64 has an output gear 66 which meshes with a gear wheel 68 secured to the drum shaft 60 so that activation of the stepping motor 64 rotatably drives the drums 56 and 58. Activation of the stepping motor 64, in turn, is controlled by medical personnel through switches 70 (FIG. 2) mounted on the housing 12 or in response to computer commands. Separate stepping motors 72 and 74 are provided for the other two lens groups 32 and 34 and each stepping motor 64, 72 and 74 may be independently activated so that the lens groups 30, 32 and 34 are independently longitudinally displaceable in the lens tube 14.

Although in the preferred embodiment of the invention a stepping motor is utilized to longitudinally displace its associated lens group 30, 32 or 34 within the lens tube 14, it will be understood that other drive means can be alternatively employed to longitudinally position the lens groups 30, 32 and 34 within the lens tube 14. For example, a manually actuated knob may be utilized in lieu of the stepping motors 64, 70 and 72 to longitudinally move the lens groups 30, 32 and 34.

Figures 9A, 9B, 9C:
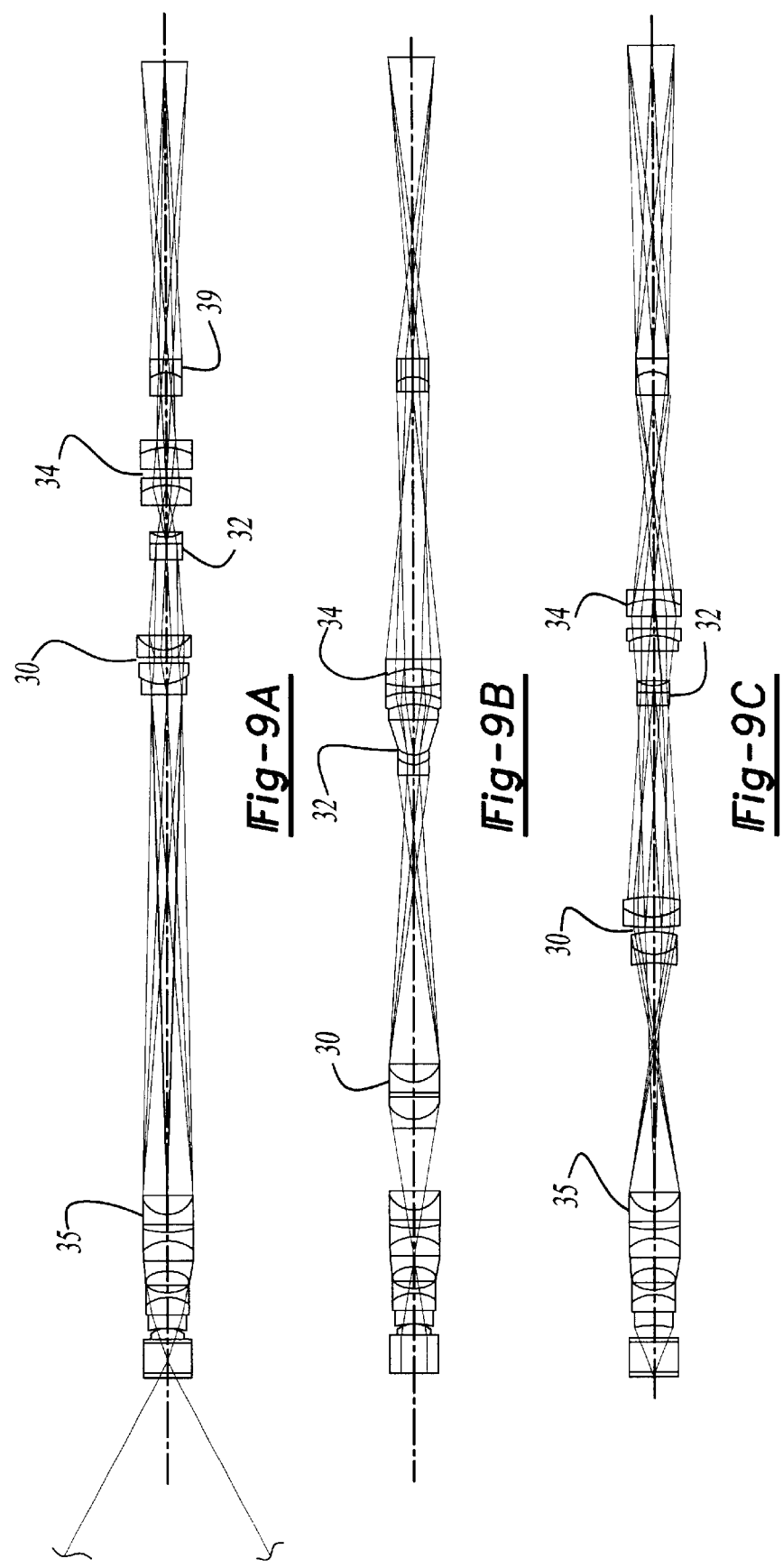
FIGS. 9A–9C are side diagrammatic views illustrating the lens magnification of the preferred embodiment of the present invention.

With reference now to FIGS. 9A–9B, the longitudinal displacement of the lens groups 30, 32 and 34 within the lens tube 14 allows the magnification achieved at the stage window 20 in conjunction with the objective lens 38 and focusing lens 39 to be varied between low or macro magnification, as shown in FIG. 9A, zero magnification (FIG. 9B) to high magnification, as shown in FIG. 9C. Typically, low or macro magnification would be utilized to position the stage window 20 against the target tissue. Once the stage window 20 is positioned against the target tissue, the lens groups 30, 32 and 34 are moved to their high magnification position for examination of the target tissue.

The shape of the lenses in each lens group 30, 32 and 34 to achieve micro to macro magnification is well known to those skilled in the art and may take any of several forms. Therefore, a further description thereof is unnecessary.

With reference now to FIG. 2, the stage 16 is detachably secured to a support block 80 by the bayonet fitting 18. The block 80, in turn, is longitudinally slidably mounted to a guide 82 which, in turn, is secured to the housing 12 and thus to the lens tube 14.

A stepping motor 84 is secured to the guide 82 and has an output shaft 86 which threadably engages a nut 88 secured to the block 80. Consequently, activation of the stepping motor 84 in turn longitudinally displaces the stage 16 relative to the lens tube 14.

Figure 5:
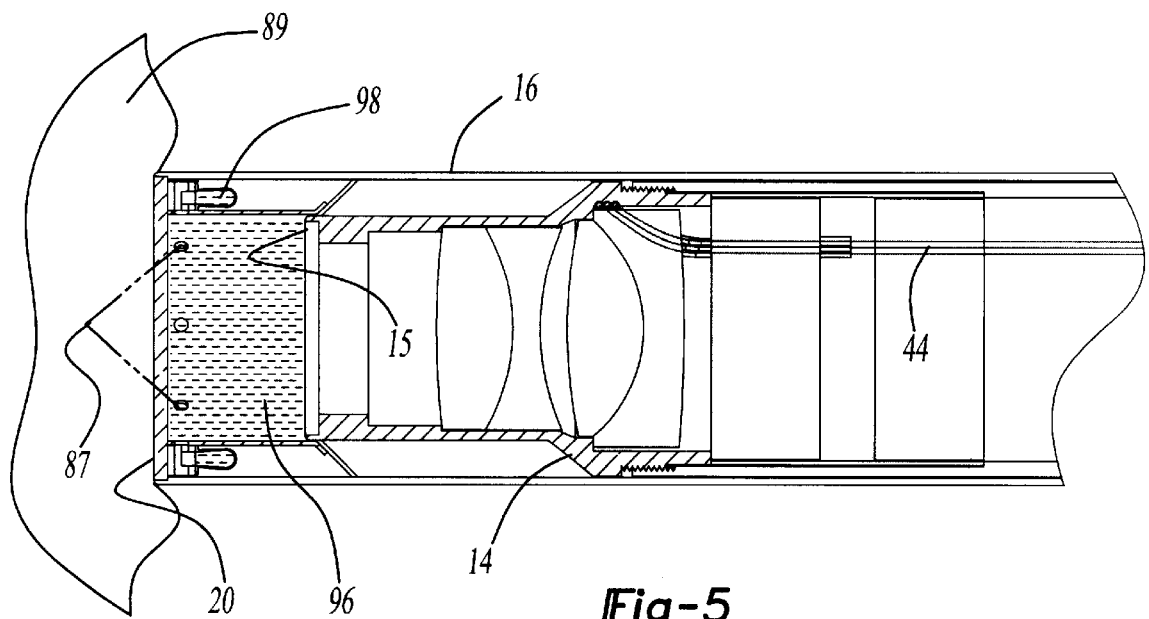
FIG. 5 is a longitudinal fragmentary sectional view illustrating a portion of the preferred embodiment of the present invention.
Figure 6:
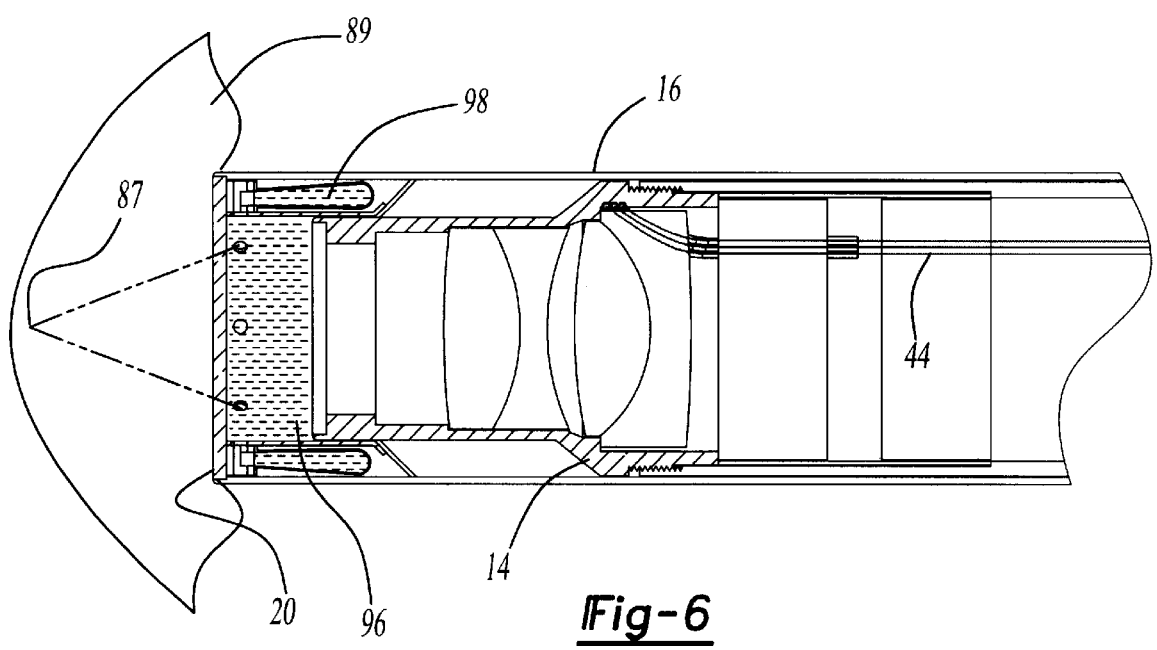
FIG. 6 is a view similar to FIG. 5, but illustrating the stage in a different position.

As best shown in FIGS. 5 and 6, the longitudinal displacement of the stage 16 relative to the lens tube 14 enables the focal point of the endoscope 10 when in high magnification to be varied to different depths within the target tissue when the stage window 20 is positioned against the target tissue 89. This in conjunction with a confocal system in the housing 12 in the optical path of the endoscope enables high magnification of the target tissue at different tissue depths.

Still referring to FIGS. 5 and 6, a fluid chamber 96 is formed between the free end 15 of the lens tube 14 and the stage window 20. This chamber 96 will necessarily change in volume as the stage 16 is longitudinally displaced relative to the lens tube 14. In order to minimize refractive errors, this chamber 96 is filled with liquid, preferably a saline solution, and the lens tube 14 is fluidly sealed to the stage 16. An annular bladder 98 contained within the stage 16 adjacent the window 20 fluidly communicates with the chamber 96 through annularly spaced ports 87. This bladder 98 expands or contracts depending upon the direction of movement of the stage 16 relative to the lens tube 14 to maintain the chamber 96 filled with the saline solution.

With reference now to FIG. 8, in order to enhance the imaging of the target tissue, preferably a source 92 of infrared radiation is provided through a beam splitter 94 through the interior of the lens tube 14 and out through the stage window 20. In practice, a diode laser having an output wavelength of 950 nanometers has proven effective in imaging body tissue.

The image from the endoscope 10 is preferably viewed from the beam splitter 94 by a graphic digitizer 102. The digitizer 102 is preferably a digital line scanning camera and provides a digital output signal to a computer system 104. The computer system 104 then displays the image on a monitor 106. The computer system 104, furthermore, is preferably programmed to colorize the image 106 as desired by the medical personnel.

In the preferred embodiment of the invention, the computer system 104 preferably electronically communicates via a network 108 to a computer system 110 remote from the endoscope 10. The communication network 108 can, for example, comprise telephone lines with modems at each computer system 104 and 110.

In practice, the computer system 104 sends the digitized images to the computer system 110 which then displays these images on its own monitor 112. The monitor 112 can, for example, be viewed by a pathologist to provide a real-time pathological examination of the target tissue without the necessity of a biopsy or removal of the patient's organ.

As a practical matter, living tissue does not remain stationary during examination. Rather, the tissue moves not only in response to movement of the endoscope, but also in response to cardiac contractions, patient breathing, etc. Consequently, in the preferred embodiment of the invention, the computer system 104 preferably captures and stores a series of sequential images upon command of the medical personnel.

Figure 10:
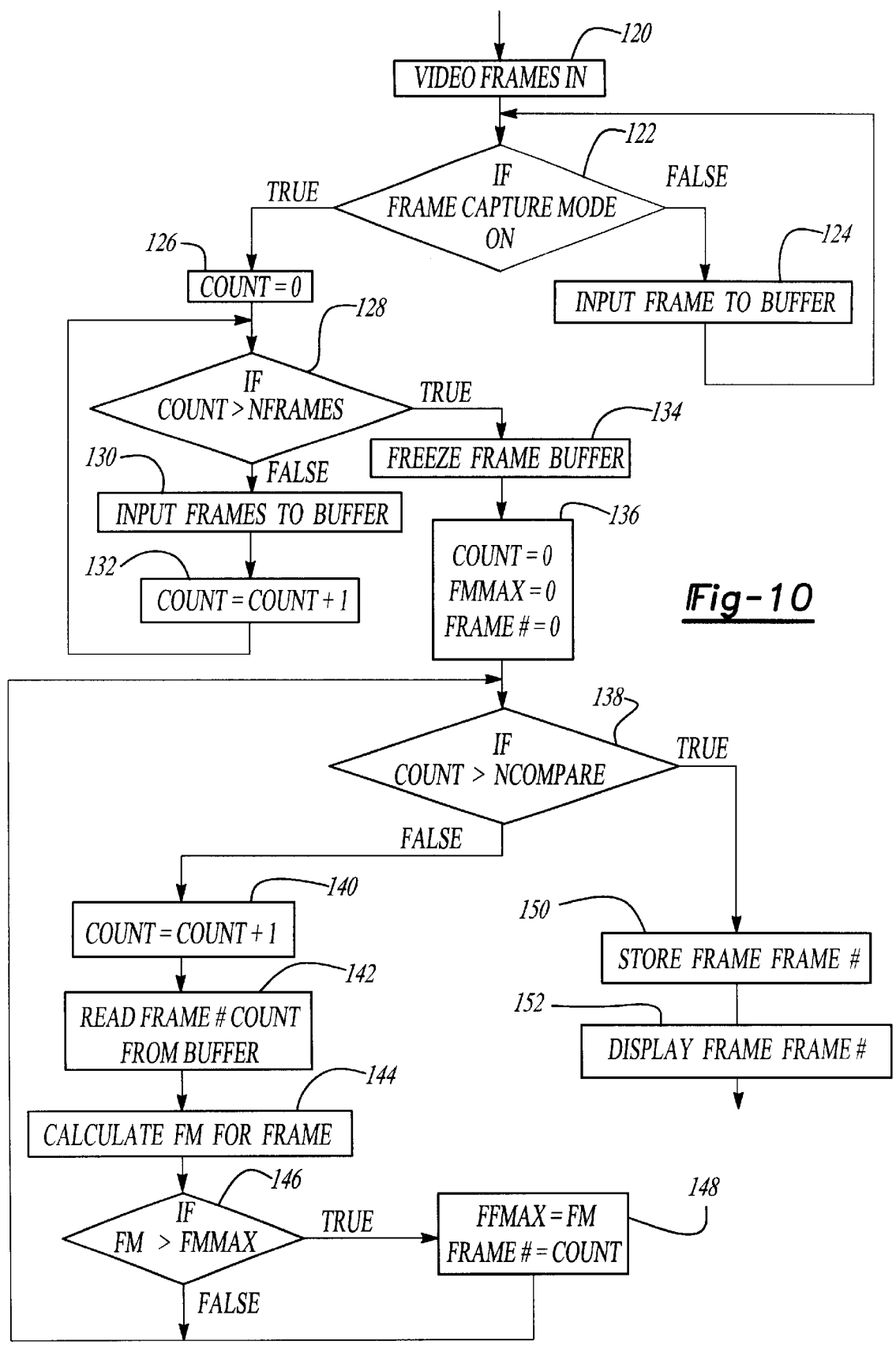
FIG. 10 is a flow chart illustrating the operation of a preferred embodiment of the present invention.

With reference now to FIG. 10, a flow chart for enhancing the video image is there shown. At step 120 a video image is received and step 120 then branches to step 122.

At step 122, the program determines if the frame capture mode is currently activated, i.e. the medical personnel has indicated that an image is desired. If not, step 122 branches to step 124 in which the current input frame is stored to a buffer and step 124 then branches back to step 122.

Conversely, assuming that the video capture mode is activated, step 122 instead branches to step 126 in which the variable COUNT is initialized to zero. Step 126 then branches to step 128.

At step 128, the program determines if the variable COUNT is greater than the variable NFRAMES where NFRAMES equals the number of video frames which are captured following activation of the capture mode. Assuming that COUNT is less than or equal to NFRAMES, step 128 branches to step 130 where the frame is input to a memory buffer. Step 130 then branches to step 132 which increments the value of the variable COUNT and step 132 branches back to step 128.

After steps 128–132 have captured the predetermined number of frames, step 128 branches to step 134 which freezes the frame buffer and then to step 136 in which the variables COUNT, FMMAX and FRAME# are all initialized to zero. Step 136 then branches to step 138.

At step 138, the variable COUNT is first compared with the variable NCOMPARE where NCOMPARE equals the number of frames compared from which to choose the capture frame. Initially, COUNT will be less than NCOMPARE so that step 138 branches to step 140 where the variable COUNT is incremented and then to step 142 where the FRAME# corresponding to the variable COUNT is inputted from a buffer. Step 142 then branches to step 144.

At step 144, the program calculates a figure of merit value FM for the frame corresponding to the variable COUNT. Various factors, such as movement of portions of the frame compared to adjacent frame captures, are determined. Step 144 then branches to step 146 where the calculated variable FM is compared to a maximum variable FMMAX. If the currently calculated variable FM exceeds the previously stored variable FMMAX (which will always occur during the first execution of step 146), step 146 branches to step 148 where the variable FMMAX is set to the value of FM and the variable FRAME190 is set to the variable COUNT. Step 148 and step 146, in the event that variable FMMAX exceeds the variable FM, both branch back to step 138.

Steps 138–148 iterate until the value of COUNT exceeds the value of NCOMPARE. At that time, the value FM has been calculated for each frame with the frame count of the maximum FM stored in the variable FRAME#. Step 138 then branches to step 150 where the selected video frame FRAME# is stored and then displayed on the monitor at step 152.

From the foregoing, it can be seen that the endoscope of the present invention permits rapid and simple adjustment of the magnification of the endoscope between macroscopic magnification and microscopic magnification. Such microscopic magnification, furthermore, allows in vivo pathological examination of tissue without a biopsy and/or removal of the organ.

A still further advantage of the present invention is that the detachable stage enables imaging at different layers and depths of the target tissue. Furthermore, since the stage is removable from the lens tube, in practice only sterilization of the stage is required in order to maintain a sterile environment in the patient's body cavity. Complete sterilization of the lens tube and housing is not required.

Having described my invention, however, many modifications thereto will become apparent to those skilled in the art to which it pertains without deviation from the spirit of the invention as defined by the scope of the appended claims.

We claim:

1. An endoscope assembly comprising:
    a housing,
    an elongated lens tube having one end secured to said housing, said lens tube adapted for insertion into a cavity of a body,
    a lens assembly,
    means for longitudinally slidably mounting said lens assembly in said lens tube between a first and a second longitudinally spaced positions in said lens tube, and
    means accessible at said housing for moving said lens assembly between said first and second longitudinally spaced positions,
        wherein said moving means comprises a bearing member positioned in said lens tube adjacent the other end of said lens tube, an elongated strand having two ends positioned in said housing, said strand extending through said lens tube and around said bearing member, said strand being connected to said lens assembly, and means for longitudinally displacing said strand in said lens tube.

2. The invention as defined in claim 1 and comprising an elongated tubular stage, said stage being open at one end and having a window disposed across its other end, said open end of said stage slidably disposed over said lens tube, and means for detachably securing said stage to said lens tube adjacent said housing.

3. The invention as defined in claim 2 wherein said detachable securing means comprises a bayonet coupling.

4. The invention as defined in claim 2 and comprising means accessible at said housing for longitudinally moving said stage relative to said housing between an extended and a retracted position.

5. The invention as defined in claim 4 wherein said window on said stage is longitudinally spaced from the other end of said lens tube thus forming a chamber between said window and said other end of said lens tube, and means for maintaining said chamber filled with a liquid.

6. The invention as defined in claim 5 wherein said maintaining means comprises a bladder disposed in said stage and open to said chamber.

7. The invention as defined in claim 2 wherein said lens assembly is a confocal lens assembly.

8. The invention as defined in claim 1 and comprising:
    a second lens assembly,
    means for longitudinally slidably mounting said second lens assembly in said lens tube between a third and a fourth longitudinally spaced positions in said lens tube, and
    means accessible at said housing for moving said second lens assembly between said third and fourth longitudinally spaced positions.

9. The invention as defined in claim 8 wherein with said first mentioned lens assembly in said first longitudinal position and said second lens assembly in said third position, said lens assemblies provide microscopic magnification and wherein with said first mentioned lens assembly in said second longitudinal position and said second lens assembly in said fourth position, said lens assemblies provide macroscopic magnification.

10. The invention as defined in claim 8 and comprising:
    a third lens assembly,
    means for longitudinally slidably mounting said third lens assembly in said lens tube between a fifth and a sixth longitudinally spaced positions in said lens tube, and
    means accessible at said housing for moving said third lens assembly between said fifth and sixth longitudinally spaced positions.

11. The invention as defined in claim 10 wherein each lens assembly comprises one or more individual lenses.

12. The invention as defined in claim 11 where said lenses for each group are respectively each secured within a first, second and third mounting tube, said mounting tubes being slidably disposed in said lens tube.

13. The invention as defined in claim 1 wherein said displacing means comprises a pair of drums rotatably mounted to said housing, one end of said strand being connected to one drum and the other end of said strand being connected to the other drum, and means for rotatably driving said drums.

14. The invention as defined in claim 13 wherein said rotatable driving means comprises an electric motor.

15. The invention as defined in claim 14 wherein said motor is a stepper motor.

16. The invention as defined in claim 13 wherein said bearing member comprises a generally U-shaped tube having its ends facing said one end of said lens tube, said strand extending through said tube.

17. The invention as defined in claim 1 and comprising means for providing illumination through said lens tube.

18. The invention as defined in claim 17 wherein said illumination means further comprises means for providing infrared illumination through said lens tube.

19. The invention as defined in claim 18 wherein said infrared illumination means comprises a laser.

20. The invention as defined in claim 19 wherein said laser is a diode laser.

21. The invention as defined in claim 20 wherein said laser has a wavelength of substantially 950 nm.

22. The invention as defined in claim 1 wherein with said lens assembly in said first longitudinal position, said lens assembly provides microscopic magnification and wherein with said lens assembly in said second longitudinal position, said lens assembly provides macroscopic magnification.

23. The invention as defined in claim 1 and comprising means for recording an image through said lens tube.

24. The invention as defined in claim 23 and comprising means for recording a plurality of sequential images viewed through said lens tube.

25. The invention as defined in claim 24 wherein said recording means comprises an electronic camera, said camera generating an output signal representative of the image viewed through said lens tube, a computer having an input, and means for connecting said camera output signal to said computer input.

26. The invention as defined in claim 25 and comprising computer means for storing said images.

27. The invention as defined in claim 25 and comprising means for electronically communicating said images to a location physically remote from the endoscope.

28. The invention as defined in claim 25 wherein said camera comprises a line scanning camera.

29. The invention as defined in claim 1 wherein movement of said lens assembly within said lens tube varies magnification through said lens tube between macroscopic and microscopic magnification.

30. The invention as defined in claim 1 and comprising confocal optics in said housing.

* * * * *